United States Patent [19]

Wallace

[11] Patent Number: 5,077,037
[45] Date of Patent: Dec. 31, 1991

[54] COMPOSITIONS FOR MAGNETIC RESONANCE IMAGING

[75] Inventor: Rebecca A. Wallace, Manchester, Mo.

[73] Assignee: Mallinckrodt Medical, Inc., St. Louis, Mo.

[21] Appl. No.: 563,225

[22] Filed: Aug. 3, 1990

[51] Int. Cl.$^5$ .................... A61K 49/00; C07C 101/26; C07F 9/38; G01N 24/01
[52] U.S. Cl. ........................................ 424/9; 424/639; 424/646; 424/647; 424/655; 128/654; 128/653.4; 534/10; 534/14; 534/15; 534/16; 549/377; 549/378; 549/415; 549/426; 549/473; 549/493; 556/40; 556/44; 556/45; 556/50; 556/56; 556/63; 556/116; 556/148
[58] Field of Search ............... 549/377, 378, 415, 426, 549/473, 493; 534/10, 14–16; 424/9, 639, 646, 647, 655; 556/40, 45, 56, 50, 63, 44, 116, 148; 128/653, 654; 536/173, 806

[56] References Cited

U.S. PATENT DOCUMENTS

| 4,647,447 | 3/1987 | Gries et al. | 424/9 |
| 4,687,658 | 8/1987 | Quay | 424/9 |
| 4,687,659 | 8/1987 | Quay | 424/9 |

FOREIGN PATENT DOCUMENTS

| 78995 | 3/1988 | Australia . |
| 1242643 | 10/1988 | Canada . |
| 250358 | 12/1987 | European Pat. Off. . |
| 3324235 | 1/1985 | Fed. Rep. of Germany . |
| 3324236 | 1/1985 | Fed. Rep. of Germany . |

OTHER PUBLICATIONS

Lauterbur, *Nature*, 242:190-1 (1973).
Damadian, *Science*, 171:1151-3 (1971).
Weinmann, et al., *AJR*, 142:619-624 (1984).
Weinmann, et al., *AJR*, 142:625-630 (1984).

*Primary Examiner*—Cecilia Shen
*Attorney, Agent, or Firm*—Evan R. Witt; Rita E. Downard

[57] ABSTRACT

Methods and compositions for enhancing magnetic resonance imaging in at least a portion of a warm-blooded animal.

16 Claims, No Drawings

COMPOSITIONS FOR MAGNETIC RESONANCE IMAGING

BACKGROUND OF THE INVENTION

This invention relates to magnetic resonance imaging agents, and more particularly to methods and compositions for enhancing magnetic resonance imaging.

The recently developed technique of magnetic resonance imaging (MRI) encompasses the detection of certain atomic nuclei utilizing magnetic fields and radiofrequency radiation. It is similar in some respects to X-ray computed tomography (CT) in providing a cross-sectional display of the body organ anatomy with excellent resolution of soft tissue detail. As currently used, the images produced constitute a map of the distribution density of protons and/or the relaxation times in organs and tissues. The technique of MRI is advantageously non-invasive as it avoids the use of ionizing radiation.

While the phenomenon of MRI was discovered in 1945, it is only relatively recently that it has found application as a means of mapping the internal structure of the body as a result of the original suggestion of Lauterbur (*Nature*, 242, 190–191 (1973)). The fundamental lack of any known hazard associated with the level of the magnetic and radio-frequency fields that are employed renders it possible to make repeated scans on vulnerable individuals. Additionally, any scan plane can readily be selected, including transverse, coronal and sagittal sections.

In an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field. According to known principles, nuclei with appropriate spin when placed in an applied magnetic field (B, expressed generally in units of gauss or Tesla ($10^4$ gauss)) align in the direct ion of the field. In the case of protons, these nuclei precess at a frequency, F, of 42.6 MHz at a field strength of 1 Tesla. At this frequency, an RF pulse of radiation will excite the nuclei and can be considered to tip the net magnetization out of the field direction, the extend of this rotation being determined by the pulse, duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual protons spins. These relaxation times have been established for various fluids, organs and tissues in different species of mammals.

In MRI, scanning planes and sliced thicknesses can be selected. This selection permits high quality transverse, coronal and saggital images to be obtained directly. The absence of any moving parts in MRI equipment promotes a high reliability. It is believed that MRI has a greater potential than CT for the selective examination of tissue characteristics. The reason for this being that in CT, X-ray attenuation and coefficients alone determine image contrast, whereas at least four separate variables ($T_1$, $T_2$, proton density and flow) may contribute to the MRI signal. For example, it has been shown (Damadian, *Science*, 171, 1151 (1971)) that the values of the $T_1$ and $T_2$ relaxation in tissues are generally longer by about a factor of two (2) in excised specimens of neoplastic tissue compared with the host tissue.

By reason of its sensitivity to subtle physiochemical differences between organs and/or tissues, it is believed that MRI may be capable of differentiating different tissue types and in detecting diseases which induce physiochemical changes that may not be detected by X-Ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of the given chemical compound is a function of the environment within which it finds itself.

In general, paramagnetic divalent or trivalent ions of elements with an atomic number of 21 to 29, 42 to 44 and 58 to 70 have been found effective as MRI contrasting agents. Suitable such ions include chromium (III), manganese (II), manganese (III), iron (III), iron (II), cobalt (II), nickel (II), copper (II), praseodymium (III), neodymium (III), samarium (III) and ytterbium (III). Because of their very strong magnetic moments, gadolinium (III), terbium (III), dysprosium (III), holmium (III) and erbium (III) are preferred. Gadolinium (III) ions have been particularly preferred as MRI contrasting agents.

Typically, the divalent and trivalent paramagnetic ions have been administered in the form of complexes with organic complexing agents. Such complexes provide the paramagnetic ions in a soluble, non-toxic form, and facilitate their rapid clearance from the body following the imaging procedure. Gries, et al., U.S. Pat. No. 4,647,447, disclosed complexes of various paramagnetic ions with conventional aminocarboxylic acid complexing agents. A preferred complex disclosed by Gries, et al., is a complex of gadolinium III) with diethylenetriaminepentaacetic acid ("DTPA"). DTPA is represented by the formula:

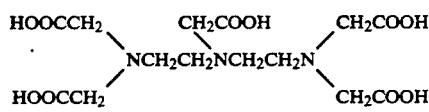

Paramagnetic ions, such as gadolinium (III), have been found to form strong complexes with ethylenediaminetetraacetic acid ("EDTA") represented by the formula:

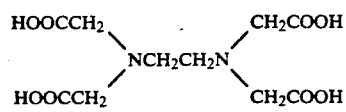

as well as with DTPA. These complexes do not dissociate substantially in physiological aqueous fluids. The complexes have a net charge of −1 or −2, and generally are administered as soluble salts. Typical such salts are the sodium and N-methylglucamine salts.

The administration of ionizable salts is attended by certain disadvantages. These salts can raise the in vivo ion concentration and cause localized disturbances in osmolality, which in turn, can lead to edema and other undesirable reactions.

Efforts have been made to design non-ionic paramagnetic ion complexes. In general, this goal has been achieved by converting one or more of the free carboxylic acid groups of the polyamino acid type ligands such as EDTA or DTPA to neutral, non-ionizable groups. For example, S. C. Quay, in U.S. Pat. Nos. 4,687,658 and 4,687,659, discloses alkylester and alkylamide derivatives respectively, of DTPA complexes. Similarly, published Dean et al., U.S. Pat. No. 4,826,673 discloses mono- and polyhydroxyalkylamide derivatives of DTPA and their use as complexing agents for paramagnetic ions.

The nature of the derivative used to convert carboxylic acid groups to non-ionic groups can have a significant impact on solubility. For example, derivatizing the carboxylic acid groups with hydrophobic alkylamide groups substantially decreases the water solubility of the complex. The solubility of the complex in physiological fluids can, in turn, effect the tissue selectivity of the complex. Hydrophilic complexes tend to concentrate in the interstitial fluids, whereas hydrophobic complexes tend to associate with cells. Thus, differences in hydrophilicity can lead to different applications of the compounds. See, for example, Weinmann, et al., *AJR*, 142, 679 (Mar. 1984) and Brasch, et al., *AJR*, 142, 625 (Mar. 1984).

Thus, a need continues to exist for new and structurally diverse ionic and non-ionic complexes of paramagnetic ions for use as MRI agents. A further need also exists in the art to develop highly stable complexes with good relaxivity and low osmolar characteristics.

SUMMARY OF THE INVENTION

The present invention provides novel complexing agents and complexes of complexing agents with paramagnetic ions. The complexes are represented by the following formula:

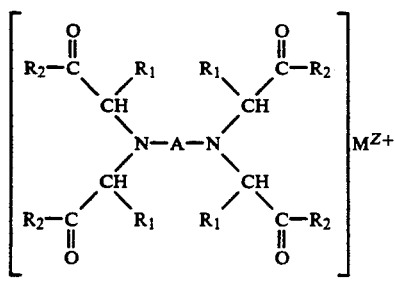

wherein A is selected from the group consisting of —CHR₃CHR₃—,

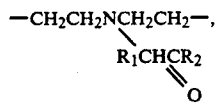

—CH₂CH₂OCH₂CH₂— and

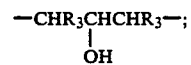

the $R_1$ groups may be the same or different selected from the group consisting of hydrogen, alkyl -such as for example methyl or ethyl wherein methyl is preferable to reduce lipophilicity, alkoxy -such as for example methoxy or ethoxy, mono- or poly- hydroxyalkyl -such as for example hydroxymethyl or dihydroxypropyl wherein dihydroxypropyl is preferred to enhance water solubility, and alkoxyalkyl such as for example methoxymethyl or methoxyethyl wherein methoxymethyl is preferred to reduce lipophilicity; the $R_2$ groups may be the same or different selected from the group consisting of —O$^{1-}$ and

the $R_3$ groups may be the same or different selected from the group consisting of hydrogen, alkyl -such as for example methyl or ethyl wherein methyl is preferable to reduce lipophilicity, alkoxyalkyl -such as for example methoxymethyl or methoxyethyl wherein methoxymethyl is preferable to reduce lipophilicity, mono- or polyhydroxyalkyl -such as for example hydroxymethyl or dihydroxypropyl wherein dihydroxypropyl is preferable to enhance water solubility, aryl -such as for example phenyl, and alkylaryl -such as for example methylphenyl whereby the $R_3$ group may be bound together in the form of a five to seven member ring; the $R_4$ groups may be the same or different selected from the group consisting of hydrogen, alkyl -such as for example methyl or ethyl wherein methyl is preferable to reduce lipophilicity, alkoxy -such as for example methoxy or ethoxy wherein methoxy is preferable to reduce lipophilicity, mono- or poly- hydroxyalkyl -such as for example hydroxymethyl or dihydroxypropyl wherein dihydroxypropyl is preferable to enhance water solubility, alkoxyalkyl -such as for example methoxymethyl or methoxyethyl wherein methoxymethyl is preferable to reduce lipophilicity, an amine -such as for example amino or methylamino, and acylaminoalkyl -such as for example acetylaminomethyl or proprionylaminomethyl; and $R_5$ is a cyclic system including one or more heteroatoms which may be the same or different selected from the group consisting of O, S, SO₂, and NR₄; $M^{z+}$ is a paramagnetic ion selected from a group of elements having atomic numbers of 21-25, 27-29, 42-44, and 58-70 and a valence, z, of 2+ or 3+; whereby the acyl, aryl and alkyl groups contain one (1) to six (6) carbon atoms and when z is 2+, two $R_2$ groups are —O$^{1-}$, and when z is 3+, three $R_2$ groups are —O$^{1-}$, and the remaining $R_2$ groups are

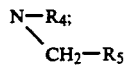

Also, disclosed is a method of performing a MRI diagnostic procedure which involves administering to a warm-blooded animal an effective amount of the above-described complex and then exposing the warm-blooded animal to a MRI procedure, thereby imaging at least a portion of the body of the warm-blooded animal.

DETAILED DESCRIPTION OF THE INVENTION

The complexing agents employed in this invention are derivatives of the well-known chelating agents, DTPA and ethylenediaminetetraacetic acid ("EDTA"). In these derivatives, free carboxylic acid groups of DTPA (those not involved in the formation of coordination bonds with the paramagnetic ion) are converted to amide groups. Thus, if the paramagnetic ion is trivalent, two of the carboxylic acid groups of DTPA or one of the carboxylic acid groups of EDTA will be derivatized to the amide form. Likewise, if the paramagnetic ion is divalent, three of the carboxylic acid groups of DTPA or two of the carboxylic acid groups of EDTA will be derivatized to the amide form. When reacted with a divalent or trivalent paramagnetic ion, the resulting complexes are substantially non-ionic and neutral.

The amide derivatives of DTPA and EDTA are prepared in a conventional manner. In general, they are prepared by reacting a stoichiometric amount of a compound having an amine group of the general formula

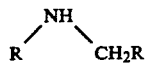

with a reactive derivative of DTPA or EDTA under amide-forming conditions. Such reactive derivatives include, for example, anhydrides, mixed anhydrides and acid chlorides. In one embodiment, the reactions are conducted in an organic solvent at an elevated temperature. Suitable solvents include those in which the reactants are sufficiently soluble and which are substantially unreactive with the reactants and products. Lower aliphatic alcohols, ketone, ethers, esters, chlorinated hydrocarbons, benzene, toluene, xylene, lower aliphatic hydrocarbons, and the like may be advantageously used as reaction solvents. Examples of such solvents are methanol, ethanol, propanol, butanol, pentenol, acetone, methylethylketone, diethylketone, methylacetate, ethylacetate, chloroform, methylenechloride, dichloroethane, hexane, heptane, octane, decane, and the like. If a DTPA or EDTA acid chloride is used as a starting material, then the reaction solvent advantageously is one which does not contain reactive functional groups, such as hydroxyl groups, as these solvents can react with the acid chlorides, thus producing unwanted byproducts.

The reaction temperature may vary widely, depending upon the starting materials employed, the nature of he reaction solvent and other reaction conditions. Such reaction temperatures may range, for example from about 0° C. to about 150° C. preferably from about 30° C. to about 70° C.

Following the reaction of the reactive DTPA or EDTA derivative with the amine, any remaining anhydride or acid chloride groups can be hydrolized to the carboxylic groups by adding a stoichiometric excess of water to the reaction mixture and heating for a short time.

The resulting DTPA or EDTA alkoxyalkylamide is recovered from the reaction mixture by conventional procedures. For example, the product may be precipitated by adding a precipitating solvent to the reaction mixture and recovered by filtration or centrifugation.

In the general amine formula

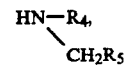

following the above process, R$_4$ may be by alkyl -such as for example methyl or ethyl wherein methyl is preferable to reduce lipophilicity, alkoxy -such as for example methoxy or ethoxy wherein methoxy is preferable to reduce lipophilicity, mono- or poly- hydroxyalkyl -such as for example hydroxymethyl or dihydroxypropyl wherein dihydroxypropyl is preferable to enhance water solubility, amine -such as for example amino or methylamino, or acylaminoalkyl -such as for example acetylaminomethyl or propionylaminomethyl, wherein the acyl and alkyl groups contain one (1) to six (6) carbon atoms. R$_5$ is a cyclic system including one or more hetero-atoms, such as for example O, S, SO$_2$, or NR$_4$. Examples of such amines include, (2-aminomethyl)tetrahydro-[2H]-furan, (2-aminomethyl)tetrahydro-[2H]-pyran, (4-aminomethyl)tetrahydro-[4H]-pyran, and (2-aminomethyl)-1,4-dioxane, whereby (2-aminomethyl)-tetrahydro-[2H]-furan commonly named tetrahydrofurfurylamine is preferred.

The paramagnetic ion is combined with the DTPA di- or trialkoxyalkylamide or EDTA mono- or dialkoxyalkylamide under complex-forming conditions. In general, any of the paramagnetic ions referred to above can be employed in making the complexes of this invention. The complexes can conveniently be prepared by mixing a suitable oxide or salt to the paramagnetic ion with the complexing agent in aqueous solution. To assure complete complex formation, a slight stoichiometric excess of the complexing agent may be used. In addition, an elevated temperature, e.g., ranging from about 20° C. to about 100° C., preferably from about 40° C. to about 80° C., may be employed to insure complete complex formation. Generally, complete complex formation will occur within a period from a few minutes to a few hours after mixing. The complex may be recovered by precipitation using a precipitating solvent such as acetone, and further purified by crystallization, if desired.

The novel complexes of this invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulation advantageously contain a sterile aqueous solution or suspension of from about 0.05 to 1.0M of a paramagnetic ion complex according to this invention. Preferred parental formulations have a concentration of paramagnetic ion complex of 0.1M to 0.5M. Such solutions also ma y contain pharmaceutically acceptable buffers and, optionally, electrolytes such as sodium chloride. Advantageously, the compositions may further contain physiologically acceptable non-toxic cations in the form of a gluconate, chloride or other suitable organic or inorganic salts, including suitable soluble complexes with a chelate/ligand to enhance safety. The chelate/ligand desirable is derived from DTPA or EDTA. Such ligands include the ligands set forth above used to complex paramagnetic and/or heavy metals to provide the complex formulations of this invention. Advantageously, the cation-ligand complex is provided in amounts ranging from about 0.1 Mol percent to about 15 Mol percent of the ligand-metal complex. Such physiologically acceptable non-toxic cations include calcium ions, magnesium ions, copper ions, zinc ions and the like including mixtures thereto. Calcium ions are preferred.

Parenteral compositions may be injected directly or mixed with a large volume parenteral composition for systemic administration.

Formulations for enteral administration may vary widely, as is well-known in the art. In general, such formulations are ligands which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging equipment being used, etc. In general, parenteral dosages will range from about 0.01 to about 1.0 mmol of paramagnetic ion complex per kilogram of patient body weight. Preferred parenteral dosage range from about 0.05 to about 0.5 MMol of the paramagnetic ion complex per kilogram of patient body weight. Enteral dosages generally range from about 0.5 to about 100 MMol, preferably from about 1.0 to about 20 MMol of paramagnetic ion complex per kilogram of patient body weight.

The novel MRI contrasting agents of this invention possess a unique combination of desirable features. The paramagnetic ion complexes exhibit an unexpectedly high solubility in physiological fluids, notwithstanding their substantially non-ionic character. This high solubility allows the preparation of concentrated solutions, thus minimizing the amount of fluid required to be administered. The non-ionic character of the complex also reduces the osmolality of the diagnostic compositions, thus preventing undesired edema and other side effects. As illustrated by the data presented below, the compositions of this invention have very low toxicities, as reflected by their high LD50 values.

The diagnostic compositions of this invention are used in the conventional manner. Compositions may be administered to a warm-blooded animal either systemically or locally to an organ or tissues to be imaged, and the animal then subjected to the MRI procedure. The compositions have been found to enhance the magnetic resonance images obtained by these procedures. In addition to their utility and magnetic resonance imaging procedures, the complexing agents of this invention may also be employed for delivery of radiopharmaceuticals or heavy metals for X-Ray contrast into the body.

The invention is further illustrated by the following examples, which are not intended to be limiting.

EXAMPLE 1

A. Preparation of N,N''-Bix[(tetrahydrofurfurylamino)-carbamoylmethyl]-diethylenetriamine-N,N',N''-triacetic acid (1)

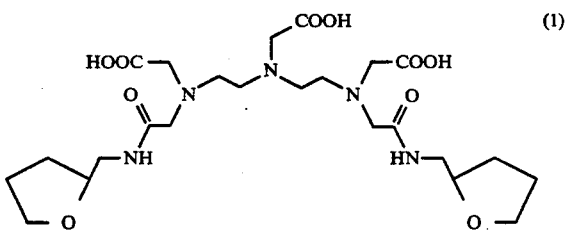

To a slurry of bis-anhydride of diethylenetriaminepentaacetic acid (80.0 g, 0.22 mole) dissolved in 1120 mL of anhydrous 2-propanol, under nitrogen atmosphere, was added a solution of tetrahydrofurfuryl amine (45.3 g, 0.45 mole) in 95 mL of anhydrous 2-propanol. The resulting mixture was heated to 60° C. under nitrogen for 20 hours. After cooling the mixture to 25° C., the white solids were filtered and washed with 2-propanol.

The white solids were then slurried in 1800 mL of hexane for 30 minutes. The solids were then again filtered and dried to give 113.8 g (0.20 mole, 91%) of N,N''-Bis[(tetrahydrofurfurylamino)-carbamoylmethyl]-diethylenetriamine-N,N',N'' triacetic acid as a white powder which was characterized as follows: mp 133°–135° C. $^{13}$C NMR (75.5 MHz, D$_2$O, ref 3-(trimethylsilyl)-propionic-2,2,3,3-d$_4$ acid, sodium salt at $\delta 0.0$):$\delta$176.0, 175.8, 172.4, 80.6, 71.3, 59.9, 57.8, 54.7, 54.3, 45.9, 31.3, 28.1. Anal. calcd for C$_{24}$H$_{41}$N$_5$O$_{10}$:C, 51.51; H, 7.39; N, 12.51. Found: C, 51.20; H, 7.59; N, 12.59.

EXAMPLE 2

B. Preparation of [N,N''-Bis(tetrahydrofurfurylamino)carbamoylmethyl)-diethylenetriamine-N,N', N''triaceto]-gadolinium III, (2)

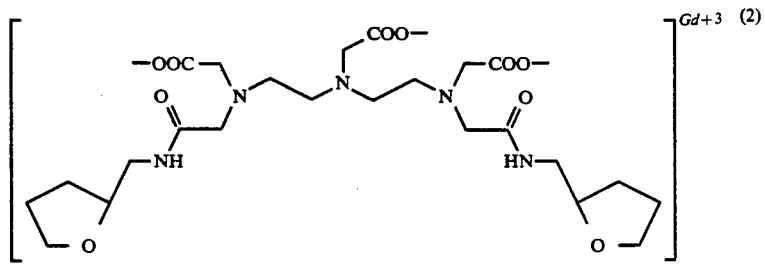

A solution of N,N''-bis[(tetrahydrofurfurylamino)-carbamoylmethyl]diethylene-triamine-N,N',N''-triactic acid, (I) (105.0 g, 0.19 mole) in 2 L of deionized water was purged with nitrogen for 30 minutes. Gadolinium oxide (32.4 g, 0.09 mole) was then added in one portion to the solution and the resulting slurry was heated at 70° C. under nitrogen atmosphere for 24 hours.

The resulting clear yellow solution was filtered through a 0.20µ Gelman membrane. The filtrate was concentrated to a volume of 200 mL and slowly added to 9 L of acetone.

Again, the resulting precipitate was filtered and then dried in a vacuum desiccator to give 110 g (0.15 mole, 81%) of [N,N″-Bis(tetrahydrofurfurylamino)carbamoylmethyldiethylene triamine-N,N′,N″-triaceto]gadolinium III as a white powder.

Further purification of this material was achieved through chromatography over reverse phase absorbent (C-18) using a Waters Kiloprep 250 system with methanol/water mixtures as eluent.

Concentration of the combined pure fractions gave a glass which was triturated with ethanol to give 60 g (0.08 mole, 44%) of [N,N″-Bis(tetrahydrofurfurylamino)carbamoylmethyldiethylene triamine-N,N′,N″-triaceto]gadolinium III as a white powder characterized as follows: HPLC chromatographic purity 99.7%, Mpt.>345° C. Anal. calcd for $C_{24}H_{38}N_5O_{10}Gd \cdot H_2O$: C, 39.39; H, 5.51; N, 9.57; Gd, 21.49. Found: C, 39.43; H, 5.65; N, 9.54: Gd, 20.89.

The mouse i.v. $LD_{50}$ value of a 0.5M solution of [N,N′-Bis(tetrahydrofurfurylamino)carbamoylmethyldiethylene triamine-N N′,N″-triaceto]gadolinium III was determined to be 16.2 mmol/kg (confidence limit of 14.3–18.4 mmol/kg) and the relaxivity rates ($mmol^{-1} sec^{-1}$) were obtained using the Bruker NMR MiniSpec (20 MHz) Spectrometer at 40° C. in both sterile water for injection (SWFI) and 4% human serum albumin (HSA): $T_1$: SWFI, 4.4; HSA, 4.8; $T_2$: SWFI, 5.6; HSA, 4.8.

As various changes could be made in the above compounds and methods without departing from the scope of the invention, it is intended that all matter contained in the above description or shown in the accompanying drawings shall be interpreted as illustrative and not in a limiting sense.

What is claimed is:

1. A complex comprising the following formula:

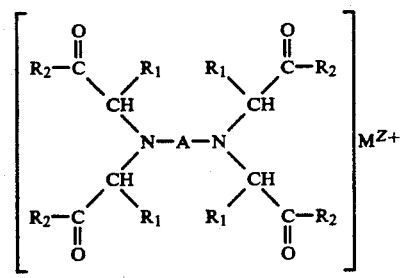

wherein A is selected from the group consisting of —$CHR_3CHR_3$—,

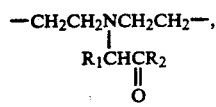

—$CH_2CH_2OCH_2CH_2$— and

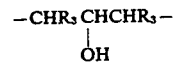

the $R_1$ groups may be the same or different selected from the group consisting of hydrogen, alkyl, alkoxy, monohydroxyalkyl, polyhydroxyalkyl and alkoxyalkyl; the $R_2$ groups may be the same or different selected from the group consisting of —$O^{1-}$ and

the $R_3$ groups may be the same or different selected from the group consisting of hydrogen, alkoxyalkyl, mono- or polyhydroxyalkyl, alkyl, aryl and alkylaryl whereby the $R_3$ groups may be bound together in the form of a five to seven member ring; the $R_4$ groups may be the same or different selected from the group consisting of hydrogen, alkyl, alkoxy, monohydroxyalkyl, polyhydroxyalkyl, alkoxyalkyl, amino and acylaminoalkyl; and $R_5$ is a cyclic system having a five to six member heterocyclic ring including one or more heteroatoms which may be the same or different selected from the group consisting of O, S, $SO_2$, and $NR_4$; $M^{z+}$ is a paramagnetic ion selected from a group of elements having atomic numbers of 21–25, 27–29, 42–44, and 58–70 and a valence, z, of 2+ or 3+; whereby the acyl, aryl and alkyl groups contain one (1) to six (6) carbon atoms, and when z is 2+, two $R_2$ groups are —$O^{1+}$, and when z is 3+, three $R_2$ groups are —$O^{1+}$, and the remaining $R_2$ groups are

2. The complex of claim 1 wherein at least one $R_2$ group is (2-aminomethyl)tetrahydro-[2H]-furan, (2-aminomethyl)-tetrahydro-[2H]-pyran, (4-aminomethyl)tetrahydro-[4H]-pyran or (2-aminomethyl)-1,4-dioxane.

3. The complex of claim 1 wherein at least one $R_2$ group is (2-aminomethyl)tetrahydro-[2H]-furan.

4. The complex of claim 1 wherein $M^{z+}$ is chromium (III), manganese (II), manganese (III), iron (III), praseodymium (III), neodymium (III), semarium (III), ytterbium (III), gadolinium (III), terbium (III), dysprosium (III), holmium (III) or erbium (III).

5. The compound N,N″-bis[tetrahydrofurfurylamino)-carbamoylmethyl]diethylenetriamine-N,N′,N″-triacetic acid.

6. The complex [N,N″-bis(tetrahydrofurfurylamino)-carbamoylmethyl]diethylenetriamine-N,N′,N″-triaceto]-gadolinium III.

7. A diagnostic composition suitable for enteral or parenteral administration to a warm-blooded animal which comprises an MRI-effective amount of a complex of a paramagnetic ion comprising the following formula:

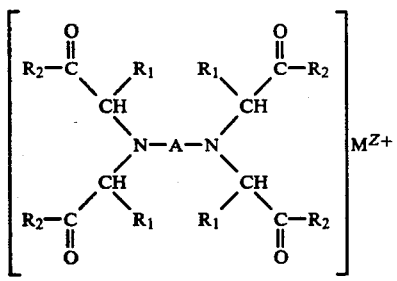

wherein A is selected from the group consisting of —CHR$_3$CHR$_3$—,

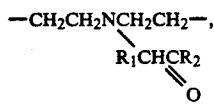

—CH$_2$CH$_2$OCH$_2$CH$_2$— and

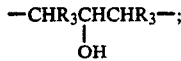

the R$_1$ groups may be the same or different selected from the group consisting of hydrogen, alkyl, alkoxy, monohydroxyalkyl, polyhydroxyalkyl and alkoxyalkyl; the R$_2$ groups may be the same or different selected form the group consisting of —O$^{1-}$ and

the R$_3$ groups may be the same or different selected from the group consisting of hydrogen, alkoxyalkyl, mono- or polyhydroxyalkyl, alkyl, aryl and alkylaryl whereby the R$_3$ groups may be bound together in the form of a five to seven member ring; the R$_4$ groups may be the same or different selected from the group consisting of hydrogen, alkyl, alkoxy, monohydroxyalkyl, polyhydroxyalkyl, alkoxyalkyl, amino and acylaminoalkyl; and R$_5$ is a cyclic system having a five to six member heterocyclic ring including one or more heteroatoms which may be the same or different selected from the group consisting of O, S, SO$_2$, and NR$_4$; M$^{z+}$ is a paramagnetic ion selected from a group of elements having atomic numbers of 21-25, 27-29, 42-44, and 58-70 and a valence, z, of 2+ or 3+; whereby the acyl, aryl and alkyl groups contain one (1) to six (6) carbon atoms, and when z is 2+, two R$_2$ groups are —O$^{1+}$, and when z is 3+, three R$_2$ groups are —O$^{1+}$, and the remaining R$_2$ groups are

and a pharmaceutically acceptable carrier.

8. The diagnostic composition of claim 7 wherein at least one of the R$_2$ groups are (2-aminomethyl)tetrahydro-[2H]-furan, (2-aminomethyl)tetrahydro-[2H]-pyran, (4-aminomethyl)tetrahydro-[4H]-pyran, or (2-aminomethyl)-1,4-dioxane.

9. The diagnostic composition of claim 7 wherein at least one R$_2$ group is (2-aminomethyl)tetrahydro-[2H]-furan.

10. The diagnostic composition of claim 7 wherein M$^{z+}$ is chromium (III), manganese (II), manganese (III), iron (III), praseodymium (III), neodymium (III), samarium (III), ytterbium (III), gadolinium (III), terbium (III), dysprosium (III), holmium (III) or erbium (III).

11. The diagnostic composition of claim 7 wherein the complex is dissolved or suspended in a sterile aqueous pharmaceutically acceptable carrier at a concentration of from about 0.05 to 1.0 M.

12. The diagnostic composition of claim 7 which further contains a pharmaceutically acceptable buffer.

13. A method of performing a magnetic resonance imaging diagnostic procedure, which comprises administering to a warm-blooded animal an effective amount of a complex of the formula:

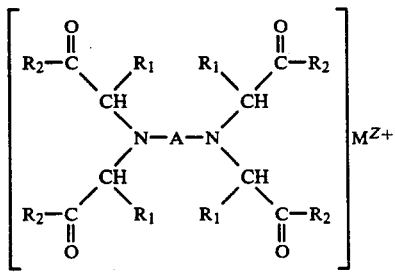

wherein A is selected from the group consisting of —CHR$_3$CHR$_3$—,

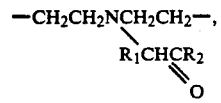

—CH$_2$CH$_2$OCH$_2$CH$_2$— and

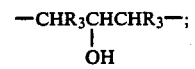

the R$_1$ groups may be the same or different selected from the group consisting of hydrogen, alkyl, alkoxy, monohydroxyalkyl, polyhydroxyalkyl and alkoxyalkyl; the R$_2$ groups may be the same or different selected from the group consisting of —O$^{1+}$ and

R$_3$ groups may be the same or different selected from the group consisting of hydrogen, alkoxyalkyl, mono- or polyhydroxyalkyl, alkyl, aryl and alkylaryl whereby the R$_3$ groups may be bound together in the from of a five to seven member ring; the R$_4$ groups may be the same or different selected from the group consisting of hydrogen, alkyl, alkoxy, monohydroxyalkyl, polyhydroxyalkyl, alkoxyalkyl, amino and acylaminoalkyl; and R$_5$ is a cyclic system having a five to six member heterocyclic ring including one or more heteroatoms which may be the same or different selected from the group consisting of O, S, $SO_2$, and $NR_4$; $M^{z+}$ is a paramagnetic ion selected from a group of elements having atomic numbers of 21–25, 27–29, 42–44, and 58–70 and a valence, z, of 2+ or 3+; whereby the acyl, aryl and alkyl groups contain one (1) to six (6) carbon atoms, and when z is 2+, two $R_2$ groups are $-O^{1+}$, and when z is 3+, three $R_2$ groups are $-O^{1+}$, and the remaining $R_2$ groups are

and then exposing the animal to a magnetic resonance imaging procedure, thereby imaging at least a portion of the body of the warm-blooded animal.

14. The method of claim 13 wherein at least one $R_2$ group is (2-aminomethyl)tetrahydro-[2H]-furan, (2-aminomethyl)tetrahydro-[2H]-pyran (4-aminomethyl)-tetrahydro-[4H]-pyran or (2-aminomethyl)-1,4-dioxane.

15. The method of claim 13 wherein at least one $R_2$ group of the complex is (2-aminomethyl)tetrahydro-[2H]-furan.

16. The method of claim 13 wherein $M^{z+}$ is chromium (III), manganese (II), manganese (III), iron (III), praseodymium (III), neodymium (III), samarium (III), ytterbium (III), gadolinium (III), terbium (III), dysprosium (III), holmium (III) or erbium (III).

* * * * *

UNITED STATES PATENT AND TRADEMARK OFFICE
CERTIFICATE OF CORRECTION

PATENT NO. : 5,077,037

DATED : December 31, 1991

INVENTOR(S) : Rebecca A. Wallace

It is certified that error appears in the above-identified patent and that said Letters Patent is hereby corrected as shown below:

Column 1, line 40,
  "direct ion" should be --direction--;

Column 2, line 43,
  "With" should be --with--;

Column 6, line 16,
  "May be by alkyl" should be --may be hydrogen, alkyl--;

Column 6, line 66,
  "ma y" should be --may--;

Column 9, line 29,
  "[N,N'-" should be --[N,N"--;

Column 10, line 35,
  "-O$^{1+}$" should be ---O$^1$---;

Column 10, line 36,
  "-O$^{1+}$" should be ---O$^1$---;

UNITED STATES PATENT AND TRADEMARK OFFICE
CERTIFICATE OF CORRECTION

PATENT NO. : 5,077,037
DATED : December 31, 1991
INVENTOR(S) : Rebecca A. Wallace It is certified that error appears in the above-identified patent and that said Letters Patent is hereby corrected as shown below:

Column 11, line 32,
  "form" should be --from--;

Column 11, line 55,
  "-0¹+"should be ---0¹---;

Column 11, line 56,
  "-0¹+"should be ---0¹---;

Column 12, line 51,
  "-0¹+"should be ---0¹---;

Column 13, line 7,
  "-0¹+" should be ---0¹---;

Column 13, line 8,
  "-0¹+" should be ---0¹---.

Signed and Sealed this

Seventh Day of September, 1993

*Attest:*

BRUCE LEHMAN

*Attesting Officer*  *Commissioner of Patents and Trademarks*